United States Patent

Bazile et al.

[11] Patent Number: 5,367,174
[45] Date of Patent: Nov. 22, 1994

[54] DEFECT DETECTING DEVICE FOR TWO-LAYER PARTS, IN PARTICULAR FOR SOLAR CELLS

[75] Inventors: Jean-Luc Bazile, Sur Siange; Paul Billon, Grasse; Patrick Mallea, Nice, all of France

[73] Assignee: Aerospatiale Societe Nationale Industrielle, France

[21] Appl. No.: 9,680

[22] Filed: Jan. 27, 1993

[30] Foreign Application Priority Data

Jan. 27, 1992 [FR] France ................ 92 00834

[51] Int. Cl.⁵ .................................. G01N 21/88
[52] U.S. Cl. ........................... 250/572; 356/237
[58] Field of Search ............. 250/562, 571, 572, 226; 356/430, 237, 448

[56] References Cited

U.S. PATENT DOCUMENTS

| | | | |
|---|---|---|---|
| 4,715,709 | 12/1987 | Sekine et al. | 250/572 |
| 4,845,374 | 7/1989 | White et al. | 356/448 |
| 4,943,732 | 7/1990 | Economou. | |

FOREIGN PATENT DOCUMENTS

| | | |
|---|---|---|
| 2641866 | 7/1990 | France. |
| 3012162 | 10/1981 | Germany. |

OTHER PUBLICATIONS

Proceedings ISTFA-80, Oct. 27, 1990, pp. 21-25.
Y. L. Chang et al., Third IEEE/CHMT International Electronic Manufacturing Technology Symposium, Oct. 12, 1987, pp. 76-80.
Patent Abstracts of Japan, vol. 12, No. 140, Apr. 28, 1988 and JP-A-62 261 045 (Hitachi Electronics) Nov. 13, 1987.

Primary Examiner—David C. Nelms
Assistant Examiner—K. Shami
Attorney, Agent, or Firm—Remy J. VanOphem

[57] ABSTRACT

A defect detecting device for checking by light reflection parts constituted by a substrate covered with a clear coat. The device includes a reference surface wherein the inspected parts are located; a polychromatic spotlight whose light beam direction intercepts the flat reference surface in an observation area, the light beam direction forming an angle larger than $\pi-\beta$, where $\beta$ is the BREWSTER angle, with the flat reference surface; a viewing apparatus whose optical axis is in the same plane as the light beam direction, the axis forming an angle larger than $\pi-\beta$ with the flat reference surface; at least a first secondary source of monochromatic light, located next to the viewing apparatus and orientated with a secondary light axis intercepting the observation area; a carriage carrying the spotlight and the viewing apparatus and the secondary source, and a device for controlling the relative displacement of the carriage with respect to the flat reference surface, in parallel with at least two scanning directions parallel to the flat reference surface.

12 Claims, 7 Drawing Sheets

DEFECT DETECTING DEVICE FOR TWO-LAYER PARTS, IN PARTICULAR FOR SOLAR CELLS

BACKGROUND OF THE INVENTION

The invention pertains to the detection of mechanical defects within substrates covered with a protective coating which is transparent to visible light. In particular it is designed to detect the presence of cracks in the semiconducting substrate of solar cells.

It is known that solar cells include a functional or effective portion composed of a semiconducting layer and usually made of silicon (this material having an absorption spectrum centered on that of the Sun), adapted to generate electric current by photovoltaic effect, from incident photons produced by the Sun. In order to protect this functional portion against external agents, it is generally covered with a clear external coating, called cover-glass. Particularly in the case of solar cells which are part of solar generators designed for use in space on spacecrafts, it is important to be able to check the good operating condition of these cells, namely to check these cells' capability to generate electric energy: it is therefore necessary to be able to detect possible mechanical defects (such as cracks), in the semiconducting layers.

Likewise, in the case of satellites placed on a stationary orbit (i.e. telecommunications, air navigation monitoring, satellite-to-receiver telecasting, etc.) one knows optically reflective coatings to be applied onto radiating surfaces: these coatings are characterized by a high infrared emissivity and a low solar absorption ratio. Among these coatings, one knows rigid Optical Solar Reflectors (abbreviated as OSRs) which are made of a coating that is clear under solar rays and which are coated on their back face with a reflective silver layer constituting the functional portion of the solar reflector. In this case too, it is important to be able to predict on ground the future performance of these solar reflectors, and thus to be able to detect any possible mechanical defects (such as cracks) in the reflective silver coatings.

Whether it be solar cells or rigid optical solar reflectors, the presence of a mechanical defect practically causes the defective component to be rejected. However, since all of the mechanical defects do not equally affect the performances of the elements considered, it is interesting to be able to differentiate between critical mechanical defects justifying a reject and minor mechanical defects which little affect the performances and which do not justify, per se, a reject. In particular, mechanical defects such as cracks within the clear coating of solar cells or optical solar reflectors are much less objectionable than geometrically similar mechanical defects found in the semiconducting or reflective coatings respectively.

German Patent 3,012,162 already describes a device designed for the inspection of photovoltaic effect semiconducting components taken one by one in a small diameter beam of light. There is also known a solar cell network inspection device using an infrared microscope, as described in article "A portable, X-Y translating, infrared microscope for remote inspection of photovoltaic solar arrays" by S. E. FORMAN and J. W. CAUNT, MIT Lincoln Laboratory dealing with a lecture given at The International Symposium for Testing and Failure Analysis, Los Angeles, Calif., on Oct. 27, 1980.

As the case may be, these devices present several disadvantages, such as large dimensions, mandatory operation in infrared, complexity of operation, high cost, etc. Furthermore, they do not contemplate discriminating the mechanical defects existing in the semiconducting layer from those existing in the clear coat.

For information, in an entirely different field, U.S. Pat. No. 3,676,008 may also be mentioned as it pertains to automated optical inspection of such bodies as glazed tiles; however, its teachings do not provide the means to offset the aforementioned disadvantages.

This is the reason why, in practice, the inspection of the solar cells already installed within a satellite solar generator, in order to check for defects such as cracks in the silicon substrate or in the clear protective coat, breaking of the interconnecting pieces or welding defects, is performed either with unaided eye or with binoculars under glancing light, which sometimes leads to subjective conclusions depending notably on the state of alertness of the operator. It should be noted that this human inspection is time-consuming (averaging approximately 10,000 cells inspected weekly, with a satellite such as TV SAT comprising 40,000 solar cells) and tiresome (since the inspection is performed in the dark).

Accordingly, what is needed is a defect detecting device on a visual principle designed for the inspection of solar cells, as well as optical solar reflectors, preferably under visible light (thus simplifying the operation), while allowing simultaneous discrimination between mechanical defects found in the functional layer and mechanical defects found in the clear protective coating. The device is fast and readily automated to large dimension component networks to be inspected, while remaining altogether simple, reliable and economical. The device is also preferably adapted to detect the orientation of the possible defects.

SUMMARY OF THE INVENTION

The invention proposes for that purpose a defect detecting device for the inspection, on a light-reflection principle, of parts which comprise a substrate covered with a clear coating or layer and including:
- a reference surface wherein the parts to be checked are located;
- a polychromatic spotlight with a beam direction intercepting the reference flat surface in an observation area, the direction forming an angle larger than $\pi-\beta$ with the flat reference surface, where $\beta$ is the BREWSTER angle;
- a viewing apparatus whose optical axis lies in the same plane as the beam direction, the axis forming an angle larger than $\pi-\beta$ with the flat reference surface;
- at least one first secondary source of monochromatic light, located next to the viewing apparatus and orientated along a secondary light axis intercepting the observation area;
- a carriage carrying the spotlight, the viewing apparatus and the secondary source, and means for controlling relative motion of the carriage with respect to the flat reference surface, paralleling at least two scanning directions which are parallel with the flat reference surface.

According to preferred features of the invention, possibly combined with one another, a second secondary monochromatic light source is provided next to the viewing apparatus, opposite from the first secondary source with reference to the plane of the beam direction and of the optical axis, the first and second secondary sources having separate light spectra.

The axes of the first and second secondary sources form a 45° angle with the plane of the beam direction and of the optical axis of the viewing apparatus.

The secondary sources respectively beam out a red and a green light.

The projections of the axes of the secondary sources over the plane of the beam direction and of the optical axis of the viewing apparatus are merged and define angles between 33° and 45° with the flat reference surface.

The spotlight includes at least one halogen lamp, and may be provided with a diffuser.

The clear coating is made of glass and the angles formed by the beam and by the optical axis of the viewing apparatus with the flat reference surface are between 33° and 45°.

The angles formed by the beam direction and by the optical axis of the viewing apparatus with the flat reference surface are equal.

The spotlight and the viewing apparatus are tilt adjustable on the carriage, and the carriage may be rotated about an axis perpendicular with the reference flat surface.

The viewing apparatus is a CCD type camera connected with a digital image processing unit which is connected with a central unit which is connected with the carriage control means.

The purpose, features and advantages of the invention are described hereunder as a non-exhaustive example with reference to the attached drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENT

Figure 1:
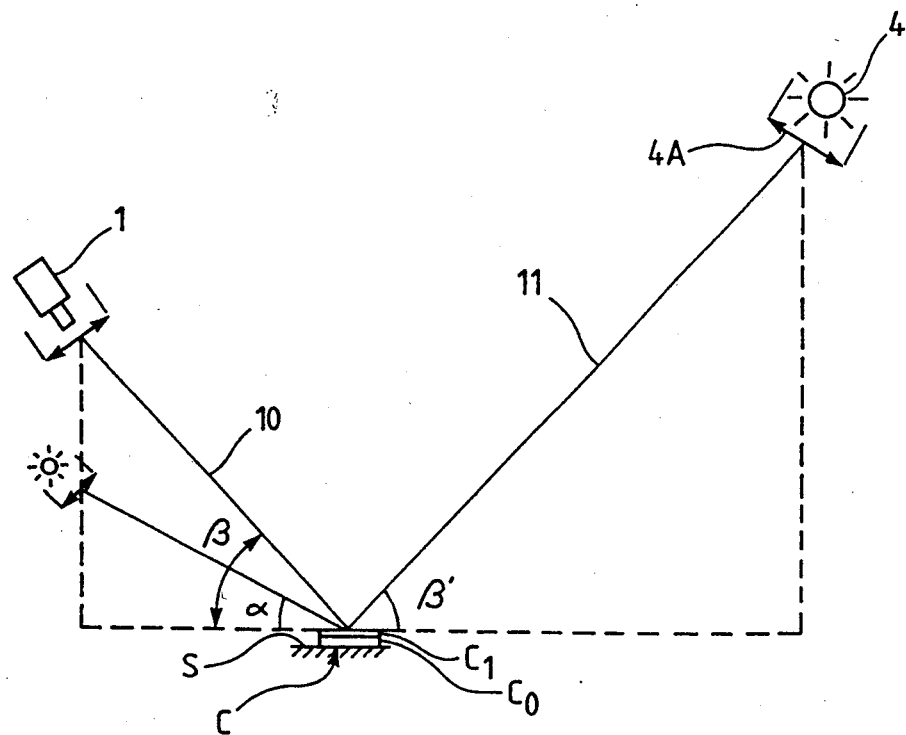
FIG. 1 is a schematic side view of a defect detecting device in accordance with the invention designed for the inspection of a solar cell.

FIG. 1 illustrates a solar cell C, comprised of a substrate $C_0$ and of a protective clear coat $C_1$. This cell rests on a flat reference surface S.

The detection of defects in one or the other of these coats is obtained by reflectometry.

Various tests have been conducted, in various operating conditions, in particular lighting conditions. Their results may be summarized as follows.

Under an exclusively ultraviolet lighting and with a full apparatus aperture (of 2.8), it is possible to obtain a good distribution of the lighting (that is uniform lighting) over the cell, with however a mediocre definition of the two types of defects considered (crack in the silicon substrate or within the clear coat) as well as a blurry picture around the perimeter of the vision field. When the aperture is closed (closure number of 16) a more concentrated light beam is obtained which improves the definition of both types of defects, as well as picture clarity. When the UV source and the considered cell are separated by a diffuser (which may consist of a single paper sheet), it is possible to obtain a good picture, after closing the aperture (number of 22), of the silicon substrate defects with loss in sharpness of defects within the clear coat (low contrast with reference to the background consisting of the cell itself); however, by reducing the aperture to 11, it is possible to obtain a higher definition of the clear coat defects while sacrificing the substrate definition visibility.

Under cold light produced by a halogen source (large emission spectrum in the visible range) and combined with fiber optics, a shutter aperture (of 22) leads to a near zero visibility and to a poor light distribution, whereas a full aperture allows for a better distribution and for the observation of defects within the clear coat. The inclusion of a diffuser (such as a simple soft plastic sheet) leads to a good observation of defects within the clear coating, at a closed aperture (of 22), and to a good light distribution but in a reduced field of vision. With a 5.6 aperture, and by bringing nearer the ends of the fibers forming the cold source, it is possible to observe a defect in a substrate (as evidenced by wide stripes, easily noticeable among the thin solid lines produced by the layer defects).

Using a neon source (neon being known as producing diffused light), an aperture of 2.8 leads to a uniform distribution and to a satisfactory view of the defects in the clear coat, whereas an aperture of 16 impairs the light distribution and the definition of the defects in the clear coat.

Finally, using a direct light source located on the side of the viewing apparatus, it is possible to observe a defect in the clear coat but with a poor definition since the image of this defect originates in the reflection of the clear coat. If a red filter is interposed at the outlet of this light source, the defect appears in a red color, and with a better definition than above. With the addition of a polychromatic spotlight provided with a diffuser, facing the viewing apparatus and lighting the whole cell, it is possible to eliminate the red color of the cell, while the defect, still colored red, remains quite visible.

A third source of light provided with a green filter is situated on the other side of the viewing apparatus from the second source of light provided with the red filter. This particular lighting configuration would result in the defects in the clear coating which lie in the same plane as the beam axis of the light source provided with the red filter to be colored green, and the defects in the clear coating lying in the same plane as the beam axis of the light source provided with the green filter to be colored red. It is thereby possible to determine the orientation of the clear coat defects with reference to the aforesaid beam axes. With an aperture of 16, the defect of the clear coat appears clearly but the light is poorly distributed; a wider aperture (of 4) leads to a better distribution of the light and to a good view of the defect but with a lesser sharpness. An aperture of 22, however, allows for the observation of the defects present in the substrate and of the defects in the clear coat. If the spotlight intensity is increased (such as 1,000 W), both types of defects appear at an aperture of 5.6 but with a lesser definition with respect to the rest of the cell.

The tests have been performed using a "HASSEL-BLAD" camera, equipped with a viewfinder designed for POLAROID cameras, a 55 zoom and a $6 \times 6$ cm² type L "KODAK" film for artificial light.

This is the configuration, with a diffuser equipped spotlight facing the viewing apparatus and two sources, respectively red and green, located on either side of the apparatus, which has been retained as being able to meet the requirements of the invention.

Figure 2:
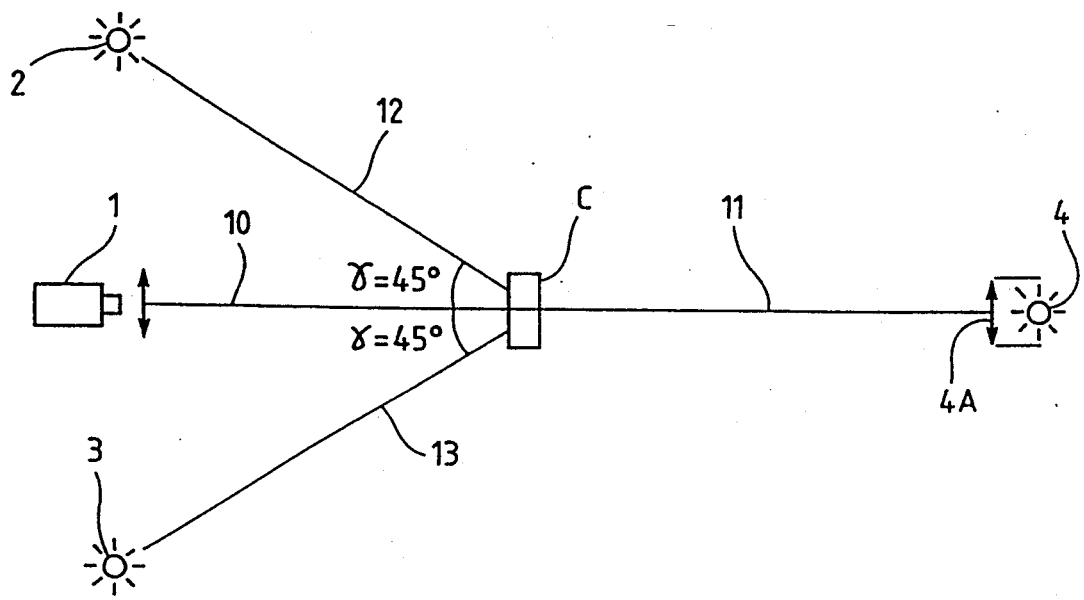
FIG. 2 is a top view thereof.

Such a configuration is illustrated in FIGS. 1 and 2, which are respectively a side view and a top view thereof, and includes a viewing apparatus 1, two spotlights 2 and 3 respectively red and green, and a spotlight 4 equipped with a diffuser 5. An optical axis 10 of the apparatus 1 and an optical axis 11 of the assembly of the spotlight 4 and the diffuser 5 lie in a same plane (vertical in practice) and form angles $\beta$ and $\beta'$ with the plane of cell C to be inspected, the plane being perpendicular to the plane of the aforementioned axes, horizontal in practice. These axes converge toward this cell. Optical axes 12 and 13 of spotlights 2 and 3, which converge with the aforementioned axes, form angles which are preferably equal, both with the plane of the cell C (angle $\alpha$) and with the plane of the axes 10 and 11 (angles $\tau$ and $\tau'$, preferably equal to 45°).

Figure 3:
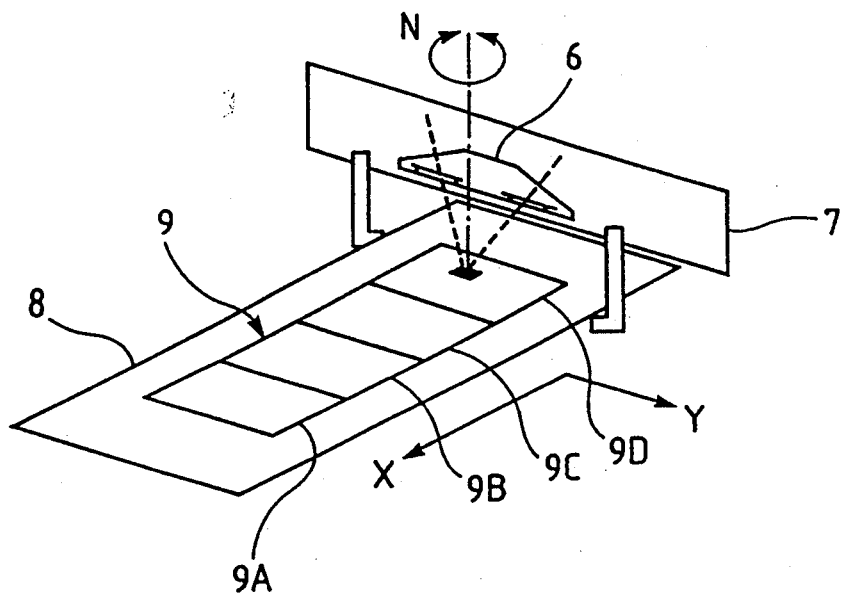
FIG. 3 is a schematic perspective view of a complete version of this apparatus, applicable to the inspection of a bi-dimensional part network.

The components 1 to 5 are preferably carried on a carriage, schematically illustrated as 6 in FIG. 3, which moves along a direction Y, on a gantry 7 moving along a direction X, in practice perpendicular to Y, these directions being parallel with the plane of the cell and more precisely with the plane of a test bench, schematically illustrated as 8 and which supports a solar generator panel 9, all of whose cells are to be inspected. As illustrated in FIG. 3, the panel is made of four sections, 9A, 9B, 9C and 9D which are traditionally connected to each other by joints in order to allow the panel to be folded for storage.

The carriage 6 is preferably orientable around the line N, normal to the X-Y plane at the location where each cell is controlled, whereby a defect which is not at all or hardly detectable in a nominal configuration of the carriage may be easily detected after rotation.

The spotlight 4 is, in a low power version, made of two 250 W, 24 V halogen lamps, side by side advantageously complemented with a calorific filter 20 and by a fan 21, in a view to eliminate distortions of the diffuser. This eliminates the chance of the cells cracking which may be induced by the lamp generated heat; the distance between the diffuser and the cell may be reduced to approximately 15 cm.

In a higher-power version, including two 1000 W, 220 V halogen lamps, it is possible to set the aperture (at a maximum of 22) and save on shutter speed; in this case, a better distribution of light is obtained but may result in distortions of the diffuser 5.

The fact that the spotlight 4 is subdivided into two lamps side by side has the advantage of enlarging and flattening the incident light cone intercepting the cells.

The spotlight 4 is desirably equipped with a focusing lens 4A offering a beam parallel with the optical axis 11. A variation thereof may be composed of a simple lens equipped with a frosting screen, thus acting as a diffuser.

In practice, it is possible to vary the diaphragm within the 22-8 range.

The diffuser allows for a uniform lighting over an area equivalent to that of a complete cell, typically 40 mm$\times$40 mm. It may be made of clear plexiglass, of plastic caulking paper or of white paper. It is white in order to constitute a neutral filter for the white light produced by the halogen lamps.

From a geometrical point of view, the diffuser is perpendicular to the axis 11.

The angles $\beta$ and $\beta'$ of FIG. 1 must meet a number of requirements.

Indeed, in order to detect the substrate defects with a certain sharpness, it is necessary to illuminate the cell with an incidence $\beta'$ as low as possible. However, if this incidence $\beta'$ is too low, the light cannot penetrate the clear coat due to the total reflection on the external surface of the coat: this incidence must therefore be higher than $\beta o = \tau - \beta$ where $\beta$ is the BREWSTER angle defined by:

$\beta$ = Arc tan ($n_2/n_1$) where $n_2$ is the clear coat material refraction index and $n_1$ is the air refraction index, ($n_1 = 1$).

In the frequent case where the clear coat is made of glass, $n_2 = 1.5$ and $\beta = 56.3$.

In order to illuminate the possible substrate defects, $\beta'$ must therefore be higher than $\beta o = 33.7$:

In practice $\beta'$ will be within the 34°-45° range, and preferably between 33° and 40°.

It is desirable to have $\beta = \beta'$. Likewise, $\alpha = \beta'$ is also desirable.

Although the above described tests were conducted with a camera, the viewing apparatus 1 is preferably a Charge Coupled Device, CCD, matrixing camera, able to send a signal applicable to a signal processing unit.

For a 512$\times$512 pixel CCD matrix with a 30 $\mu$m mesh in order to fully observe a 60 mm$\times$60 mm cell, with a 30 cm distance between the observation area (cell) and the lens, the apparatus is preferably equipped with a 75 mm lens, 30 mm in diameter, image angle 12°. This is for example the 12S camera, available from C.C.C.

Figure 4:
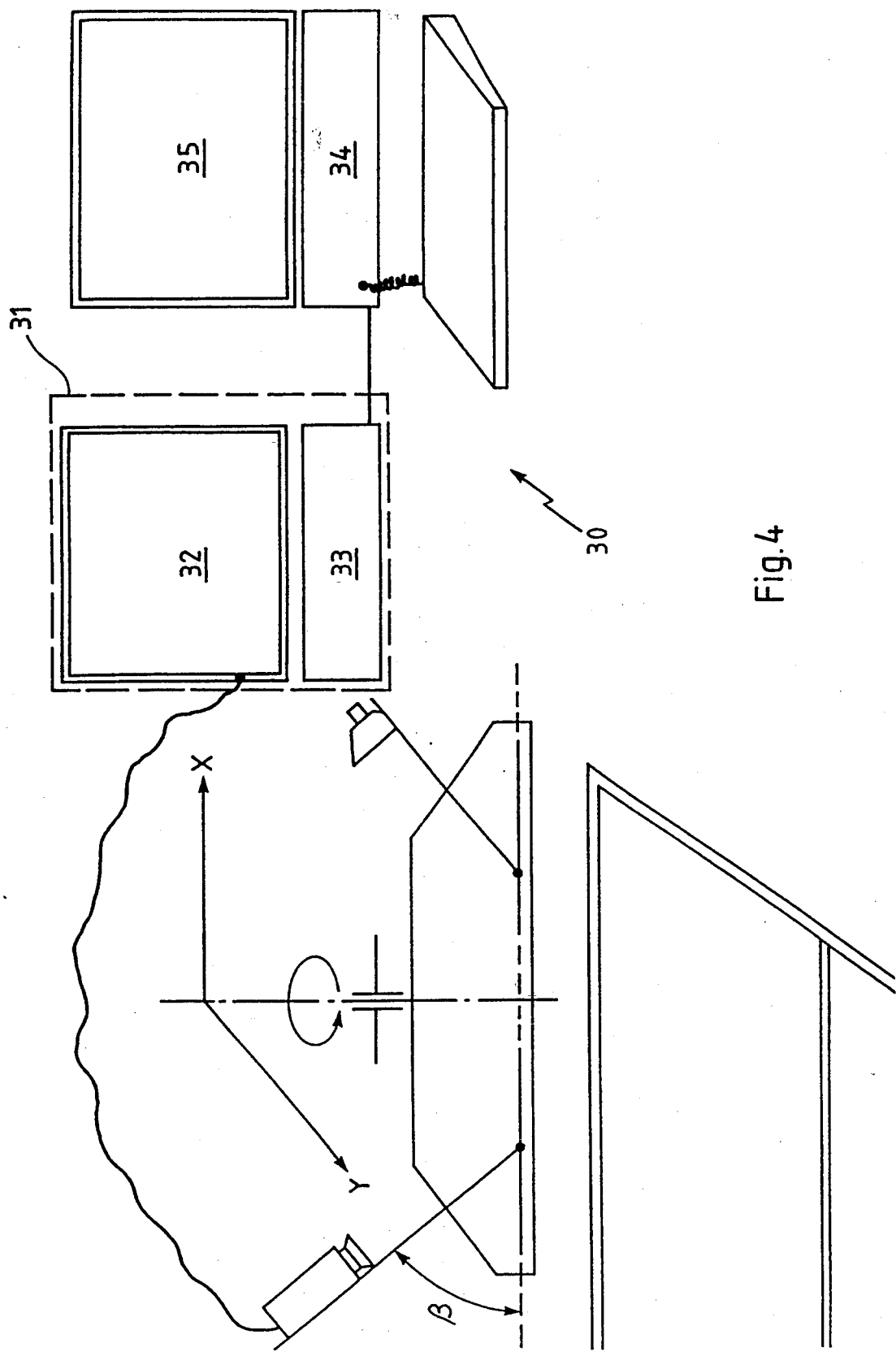
FIG. 4 is a schematic view of the image processing system.

FIG. 4 schematically illustrates the construction of the processing system 30, connected with the camera 1. It includes:

an image acquisition unit 31, adapted to receive and size the image in digital form, from signals transmitted by the viewing apparatus. It includes an image display unit 32 and a digitizing board 33;

a processing unit 34, practically consisting of a microprocessor further adapted to control the motions of the carriage 6 and of the gantry 7; and a result display assembly, such as a monitor 35 and/or a printer, not illustrated herein.

This system operates in two modes. In the automatic mode, the motions of the carriage 6 and of the gantry 7, as well as the processing of the signals sent by the viewing apparatus 1 are automatic. The processing unit causes the display assembly to print out a list of the defects with their positions in the solar generator panel 9 to be inspected. This inspection may be conducted 24 hours a day in an actually repetitive manner. In the semiautomatic mode, whereby the motions are automatically controlled and an operator performs all inspection operations on the display 35, the inspection is performed by a human, as in the past, but in far more ergonomical conditions which eliminates any needless fatigue, as is the case with uncomfortable positions and work in the darkness.

Figure 5:
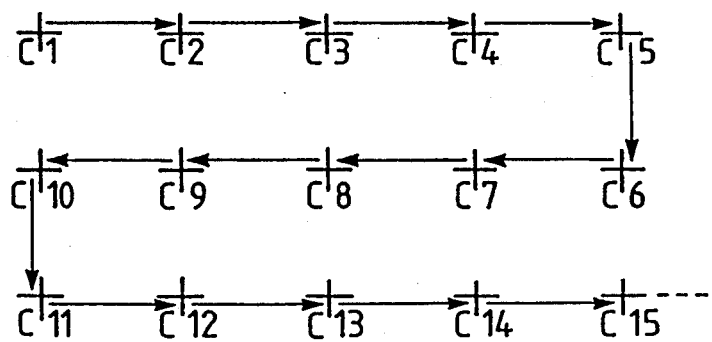
FIG. 5 is a schematic illustration of the inspection operation sequence for a group of 3×5 cells.

FIG. 5 gives an example of the inspection sequence for 15 cells numbered C1 to C15.

Figure 6:
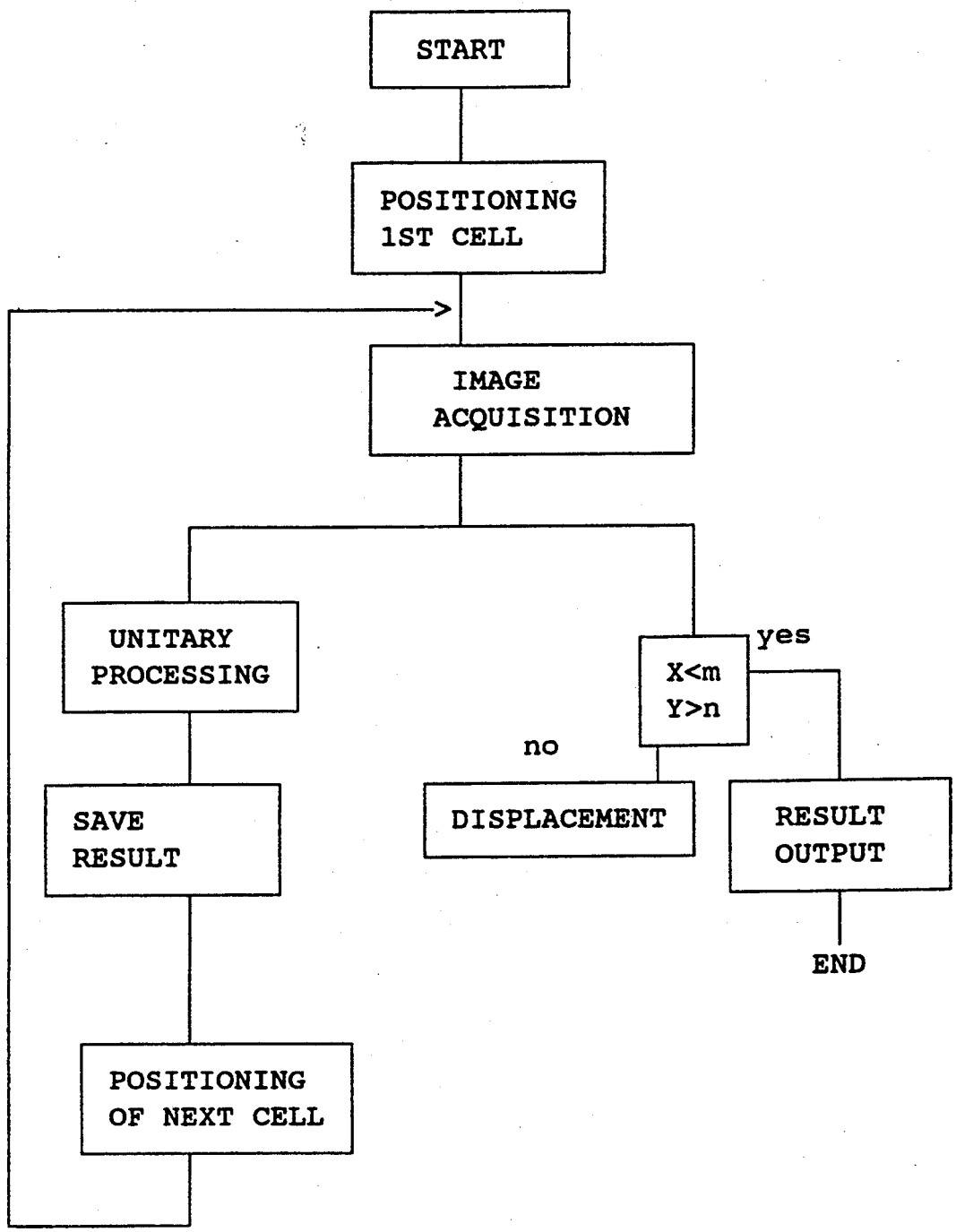
FIG. 6 is a flow chart of the general algorithm of an automated version of the system illustrated in FIG. 3.

A defect identification process is illustrated in FIG. 6 where m and n respectively identify the number of cells, per line and per column, on the panel to be checked.

The light source, consisting of one or two halogen lamps located at an adequate distance to prevent overheating of the cells, illuminates those cells with a polychromatic light beam whose diameter is large enough to cover a whole cell.

The light source and the camera are both orientated in such a way that the light is reflected toward the lens of the camera.

The camera-to-cell distance is such that the field of observation covers a whole cell; the camera field area must be lower than the illuminated area.

The aperture and light intensity are set in order to obtain a sharp picture.

For economical reasons, the results may be recorded by memorizing each component type and position.

As an example, the MORPHOPERICOLOR System sold by NUMELEC is used, which is an image analysis system encompassing the capture acquisition, digital and binary processing, as well as quantitative measurement functions.

It has to be controlled by a host computer, which is an IBM PC or compatible in the present case.

The main feature of the MORPHOPERICOLOR resides in its speed since it performs an erosion type neighborhood (side-by-side) operation, within a total of 6.5 ms for an image of 256×256 pixels or 26 ms for a size of 512×512, thus offering a power of 10M erosion/second.

These performances make it particularly efficient for complex image analysis and viewing operations which generally require a response time in the order of one second.

Acquisition function:

The MORPHOPERICOLOR includes a video real-time image acquisition board in two preprogrammed formats of 256×256 and 512×512 pixels for a depth of 6 bits.

Processing function:

With an architecture of two binary processors, the MORPHOPERICOLOR System can process images on any number of bits: 6 bits or more if they are sent by a host computer and by any other recorder than the video camera. The processing time is directly proportionate to the depth of bits used, within the limits of the system memory of 1.2 mega bytes.

Example:

| | |
|---|---|
| a 6 bit digital erosion in a 256 × 256 format is obtained in | 120 ms |
| a 6 bit digital convolution in a 256 × 256 format is obtained in | 300 ms |
| a 6 bit digital histogram in a 256 × 256 format is obtained in | 320 ms |

In binary image:

| | |
|---|---|
| an erosion, in the 256 ' 256 format, is accomplished in | 6.5 ms |
| a 100 × 100 square skeletalizing in a 256 × 256 format is accomplished in | 1 sec. |
| a length of 100 is smoothed in | 650 ms |

Measuring function

The individual analysis measurement operations:
Area
Perimeter
Number of intercepts are performed in one pass through the processor, namely 6.5 ms in the 256×256 format and 26 ms in the 512×512 format.

The total duration is proportionate to the number of objects in the picture.

Control Software

The above processing functions are controlled from the host computer, using a dedicated language based on a FORTH core adapted to the sequential transformations which generally take place during an image analysis.

Figure 7:
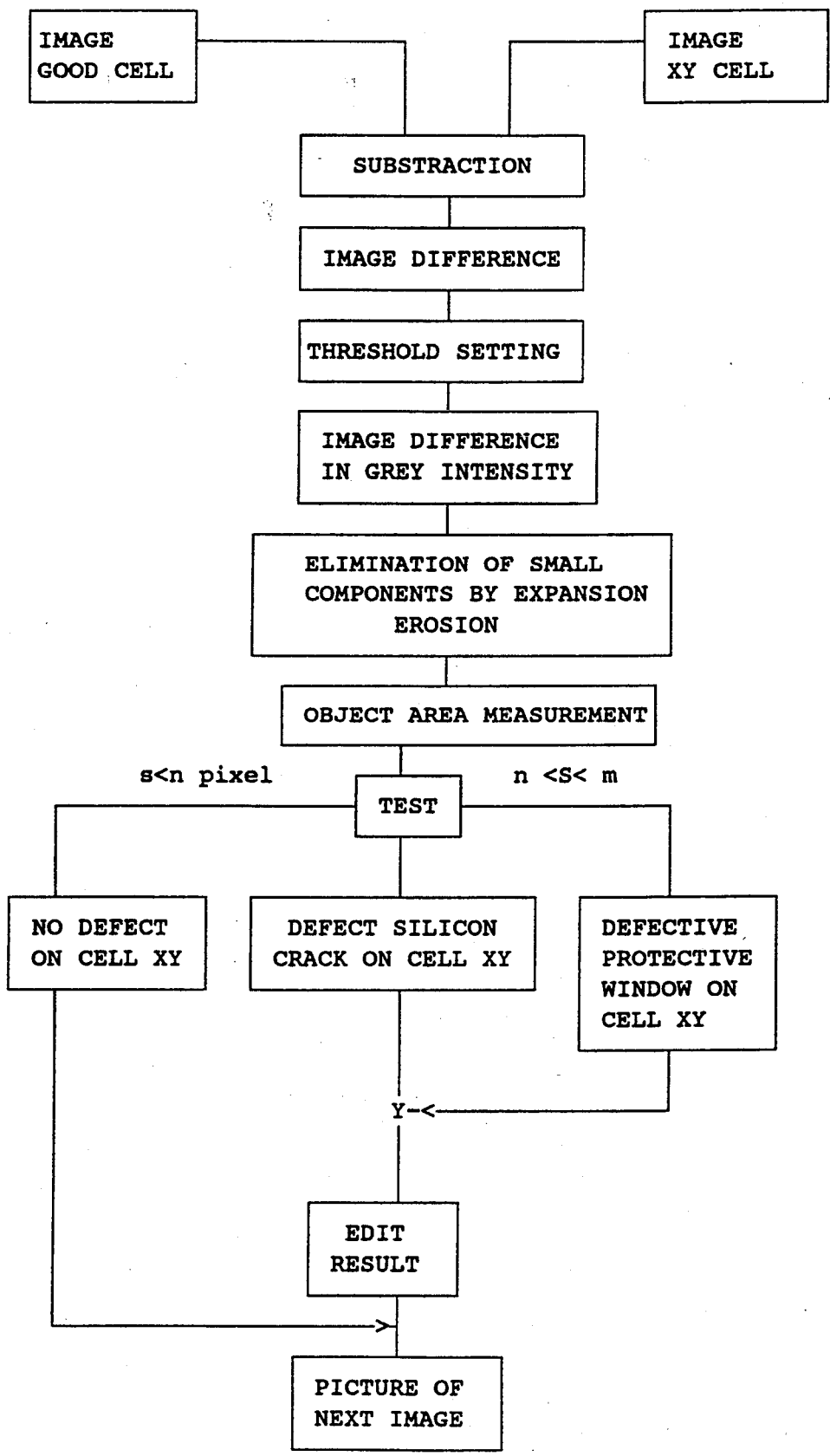
FIG. 7 is a flow chart of the processing algorithm for each image.

As an example, FIG. 7 shows a classical processing algorithm, based on image comparison, respectively involving a defect-free control cell and the cell to be inspected.

The inspection table is for example a conventional 3-axis platform, equipped with a NUM 760 numerical control unit.

The travel of the gantry may amount to 2,800 mm, while the transverse travel of the carriage may reach 1620 mm, at a speed up to 10 m/mn.

Figure 8:
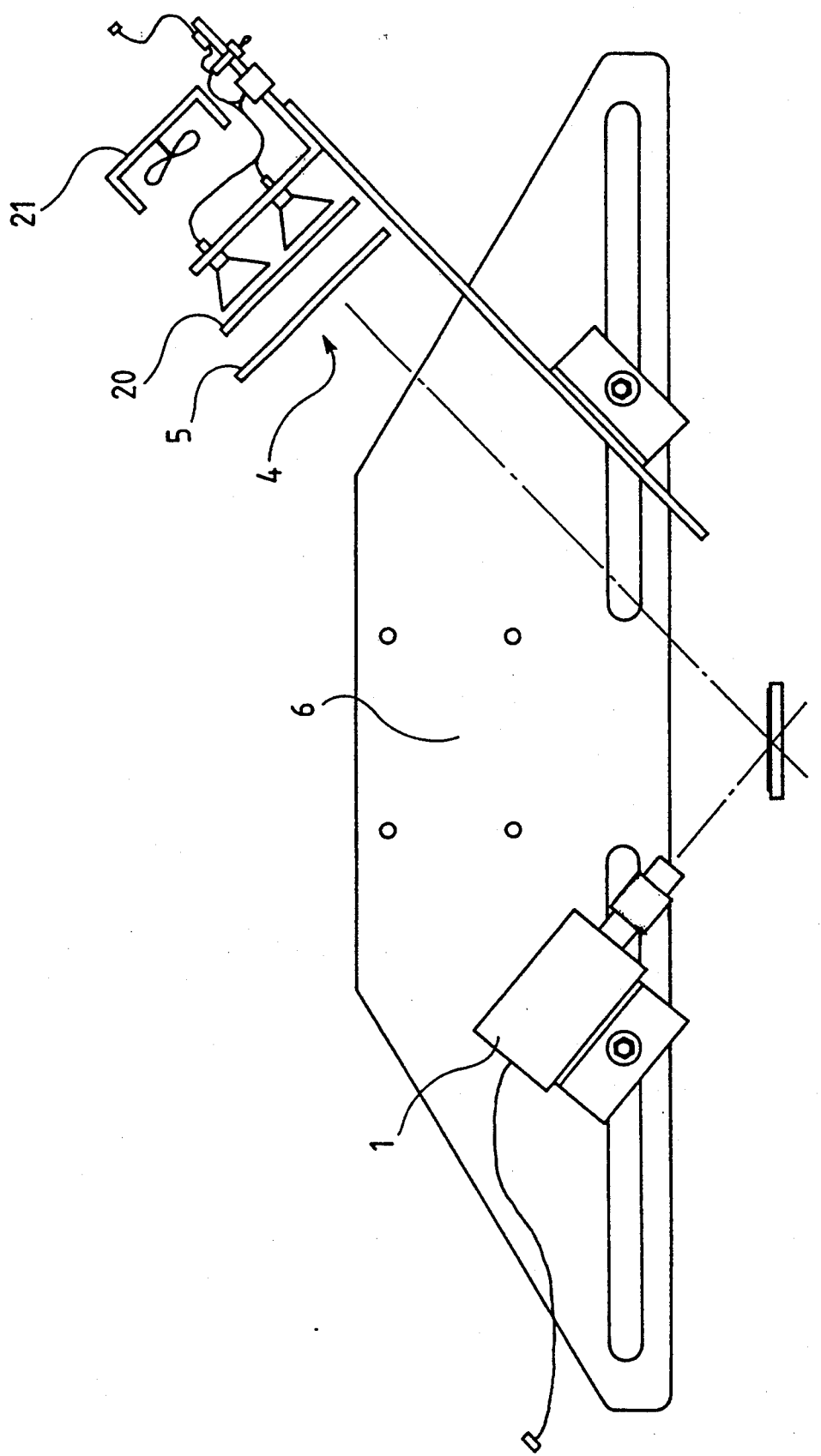
FIG. 8 is an elevational view of the carriage.

FIG. 8 is a schematic elevational view of the carriage.

The small spotlights 2 and 3 may be variable power halogen lamps. A clear PVC diffuser 5 allows for uniform distribution of the light over the surface of several cells to be inspected. In front of the spotlights, a heat absorbing filter 20 is provided to block the infrared radiation so as to avoid any heat distortion of the filter 5. Further, a cooling fan 21 is preferably provided behind the spotlights (for example 12 V) intended to evacuate the heat produced by the spotlights.

Figure 9:
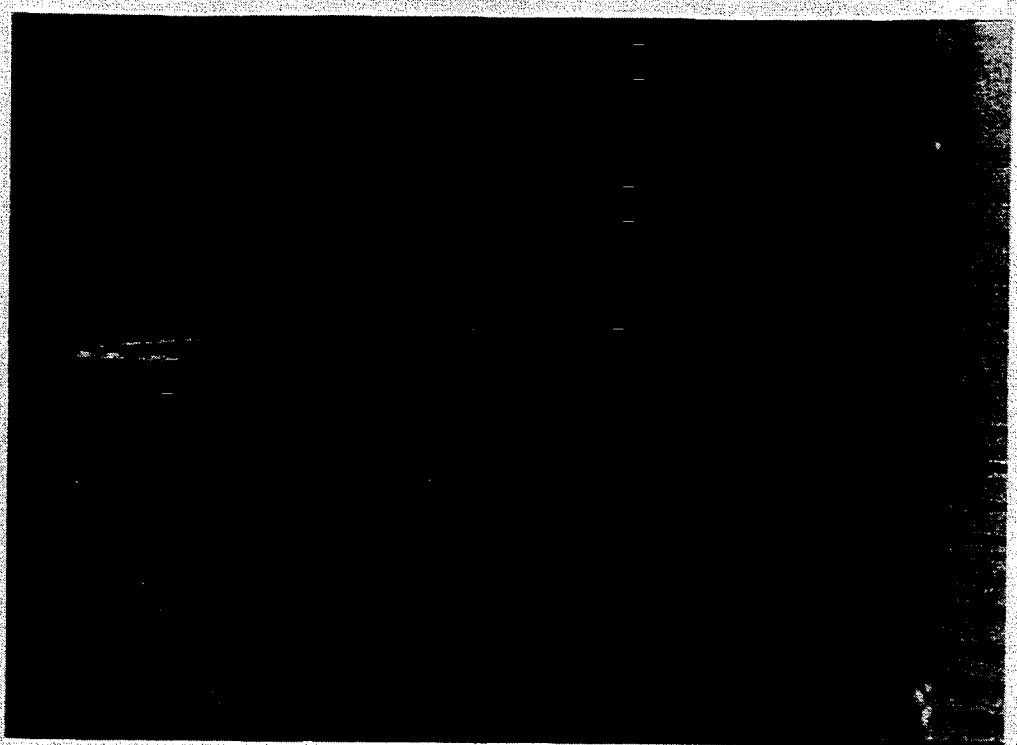
FIG. 9 is a view illustrating a defect in the clear coat of a solar cell.
Figure 10:
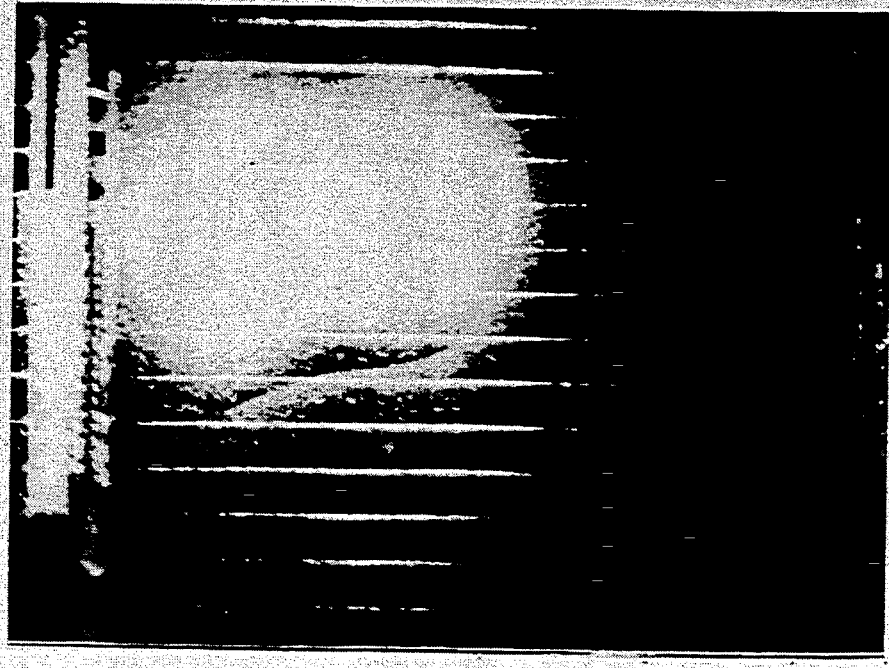
FIG. 10 illustrates a defect in the silicon substrate of the cell shown in FIG. 9.

FIGS. 9 and 10 are respective views of defects respectively located in the clear coat and in the substrate.

On these pictures, the defects in the clear coat are evidenced by solid lines, whereas the substrate defects corresponding to substantially V-shaped profiles are evidenced by contrast between the illuminated sides and the dark sides.

The foregoing description is a non limitative example of the invention and any variations thereof would still remain within the scope of the invention.

We claim:

1. A device for detecting defects in a planar substrate covered by a clear coating, said device comprising:
    a polychromatic spotlight producing a beam of polychromatic light having an optical axis, said polychromatic spotlight being placed at an observation area such that said beam of polychromatic light intercepts said planar substrate at an angle larger than $\pi$-$\beta$, where $\beta$ is the Brewster angle;
    a viewing apparatus having an optical axis lying in the same plane as said optical axis of said polychromatic beam of light, said optical axis of said viewing apparatus being at an angle larger than $\pi$-$\beta$ with said planar substrate;
    a first secondary source of monochromatic light producing a beam of monochromatic light having a secondary optical axis, said first secondary source being located adjacent said viewing apparatus, said secondary optical axis intercepting said observation area;
    a movable carriage supporting said polychromatic spotlight, said viewing apparatus, and said first secondary source of monochromatic light; and means for controlling displacement of said movable carriage relative to said planar substrate.

2. The device in accordance with claim 1, further including a second secondary source of monochromatic light having a light spectrum different than said first secondary source of light mounted on said movable carriage next to said viewing apparatus, said first and second secondary sources of monochromatic light, provided on respective sides of said viewing apparatus.

3. The device in accordance with claim 2, wherein each of said first and second secondary sources of monochromatic light produce beams of light directed at a 45° angle with respect to said optical viewing axis of said viewing apparatus.

4. The device in accordance with claim 3, wherein each of said light beams produced by said first and second secondary sources of monochromatic light are red and green lights, respectively.

5. The device in accordance with claim 3, wherein the angle of said light beams produced by said first and secondary sources of monochromatic light and the angle of said optical viewing axis are in the range of 33° to 45°.

6. The device in accordance with claim 1, wherein said polychromatic spotlight comprises a halogen light.

7. The device in accordance with claim 1, wherein said polychromatic spotlight comprises a diffuser.

8. The device in accordance with claim 5, wherein said clear coating is glass.

9. The device in accordance with claim 1, wherein the angle formed between said light beam produced by said polychromatic spotlight and said planar substrate is equal to the angle formed between said optical viewing axis and said planar substrate.

10. The device in accordance with claim 1, wherein said viewing apparatus and said polychromatic beam of light are tiltably mounted on said movable carriage.

11. The device in accordance with claim 1, wherein said carriage is rotatable.

12. The device in accordance with claim 1, wherein said viewing apparatus is a CCD camera and further comprises a digital image processing unit connected to said CCD camera.

* * * * *

UNITED STATES PATENT AND TRADEMARK OFFICE
CERTIFICATE OF CORRECTION

PATENT NO. : 5,367,174
DATED : November 22, 1994
INVENTOR(S) : Jean-Luc Bazile, Paul Billon and Patrick Mallea It is certified that error appears in the above-indentified patent and that said Letters Patent is hereby corrected as shown below:

Column 6, line 24, delete "$\tau-\beta$" insert ---- $\pi-\beta$ ----.

Column 7, line 64, delete "256' 256" insert ---- 256 x 256 ----.

Signed and Sealed this

Fourteenth Day of February, 1995

Attest:

BRUCE LEHMAN

*Attesting Officer*    *Commissioner of Patents and Trademarks*